(12) United States Patent
Boysset et al.

(10) Patent No.: US 10,874,754 B2
(45) Date of Patent: Dec. 29, 2020

(54) METHOD AND ARRANGEMENT FOR STERILIZATION AND STORAGE OF MEDICAL DEVICES

(71) Applicant: Sterilux SA, Yverdon-les-Bains (CH)

(72) Inventors: Max Boysset, Bonvillars (CH); Marc Spaltenstein, Ballaigues (CH)

(73) Assignee: Sterilux SA, Yverdon-les-Bains (CH)

( * ) Notice: Subject to any disclaimer, the term of this patent is extended or adjusted under 35 U.S.C. 154(b) by 142 days.

(21) Appl. No.: 14/765,292

(22) PCT Filed: Feb. 6, 2014

(86) PCT No.: PCT/EP2014/052367
§ 371 (c)(1),
(2) Date: Jul. 31, 2015

(87) PCT Pub. No.: WO2014/122230
PCT Pub. Date: Aug. 14, 2014

(65) Prior Publication Data
US 2016/0008498 A1   Jan. 14, 2016

(30) Foreign Application Priority Data

Feb. 6, 2013  (CH) ...................................... 0408/13

(51) Int. Cl.
*A61L 2/10* (2006.01)
*A61L 2/26* (2006.01)
(Continued)

(52) U.S. Cl.
CPC ................... *A61L 2/10* (2013.01); *A61L 2/26* (2013.01); *B65D 25/54* (2013.01); *B65D 81/18* (2013.01);
(Continued)

(58) Field of Classification Search
CPC ........................................................ A61L 2/10
(Continued)

(56) References Cited

U.S. PATENT DOCUMENTS 4,296,328 A * 10/1981 Regan ..................... C02F 1/325
250/432 R
4,390,432 A * 6/1983 Takeguchi ............. A01K 63/04
210/615
(Continued)

FOREIGN PATENT DOCUMENTS

EP           1 623 724 A1    2/2006
WO    WO 2004/031706 A1    4/2004
(Continued)

OTHER PUBLICATIONS

International Search Report for PCT/EP2014/052367 dated Apr. 10, 2014.

*Primary Examiner* — Holly Kipouros
(74) *Attorney, Agent, or Firm* — Blank Rome LLP

(57) ABSTRACT

Method of sterilization of a medical device, in particular surgical instrument, placed in a closable airtight container, including placing such medical device inside a closable airtight container; closing the container; placing a Vacuum Ultraviolet Light source against a window of said container, wherein such window is transparent to Vacuum Ultraviolet light and to UVC and/or Middle Ultraviolet light; irradiating a volume inside such closed container with Vacuum Ultraviolet Light through such window in order to generate ozone and/or ozonites within such volume; removing the Vacuum Ultraviolet Light source; and waiting for an incubation time.

34 Claims, 15 Drawing Sheets

(51) Int. Cl.
  *B65D 25/54* (2006.01)
  *B65D 81/18* (2006.01)
(52) U.S. Cl.
  CPC ... *A61L 2202/122* (2013.01); *A61L 2202/182* (2013.01); *A61L 2202/24* (2013.01)
(58) Field of Classification Search
  USPC .................................................. 422/123, 23
  See application file for complete search history.

(56) References Cited

U.S. PATENT DOCUMENTS

| | | | | |
|---|---|---|---|---|
| 5,393,419 | A * | 2/1995 | Tiede | A61L 2/10 210/192 |
| 6,028,315 | A * | 2/2000 | Bailey | A61L 2/10 250/454.11 |
| 6,565,743 | B1 * | 5/2003 | Poirier | B65D 51/00 116/284 |
| 8,048,370 | B1 | 11/2011 | Barnes | |
| 2003/0075490 | A1 * | 4/2003 | Lifschitz | C02F 1/325 210/192 |
| 2003/0133832 | A1 | 7/2003 | D'Ottone | |
| 2006/0130663 | A1 * | 6/2006 | Joshi | A61L 9/015 96/224 |
| 2007/0181509 | A1 * | 8/2007 | Araiza | A61L 9/20 210/748.11 |
| 2007/0209957 | A1 | 9/2007 | Glenn et al. | |
| 2007/0272877 | A1 * | 11/2007 | Tribelsky | A61L 2/10 250/431 |
| 2008/0131330 | A1 * | 6/2008 | Lyon | C02F 1/325 422/105 |
| 2009/0090383 | A1 * | 4/2009 | Ingleson | A61L 2/10 134/1.1 |
| 2009/0123331 | A1 * | 5/2009 | Ross | A61L 2/10 422/24 |
| 2009/0304553 | A1 | 12/2009 | Gordon | |
| 2010/0007492 | A1 * | 1/2010 | Ressler | A61L 2/10 340/540 |
| 2012/0039751 | A1 * | 2/2012 | Shenberg | A61L 2/183 422/119 |
| 2012/0056102 | A1 | 3/2012 | Stanley et al. | |
| 2013/0048545 | A1 * | 2/2013 | Shatalov | C02F 1/325 210/96.1 |
| 2013/0140244 | A1 * | 6/2013 | Barry | C02F 1/32 210/748.1 |
| 2013/0330235 | A1 * | 12/2013 | Stibich | G16H 40/20 422/105 |

FOREIGN PATENT DOCUMENTS

| | | |
|---|---|---|
| WO | WO 2004/062800 A1 | 7/2004 |
| WO | WO 2007/146699 A2 | 12/2007 |

* cited by examiner

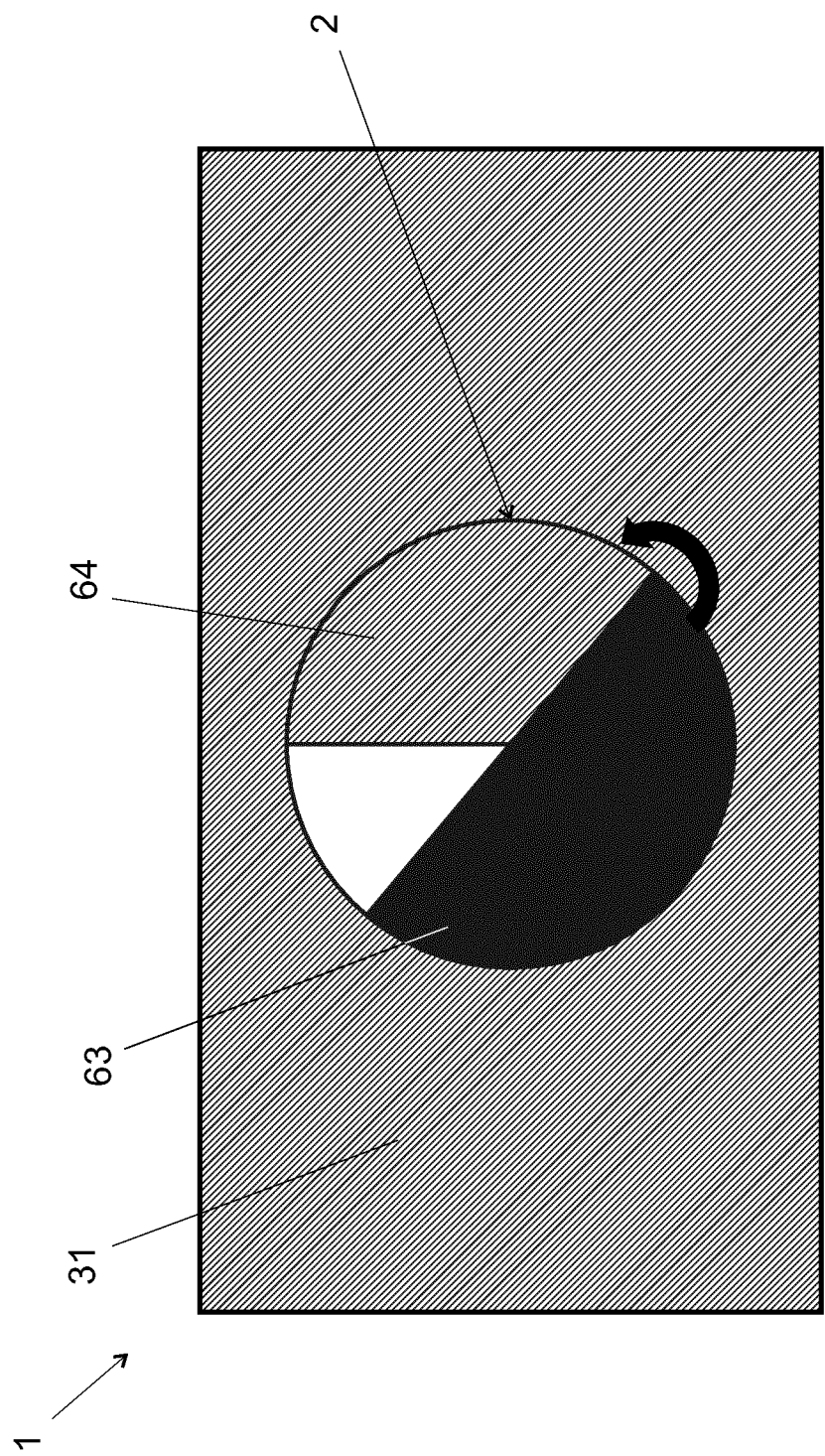

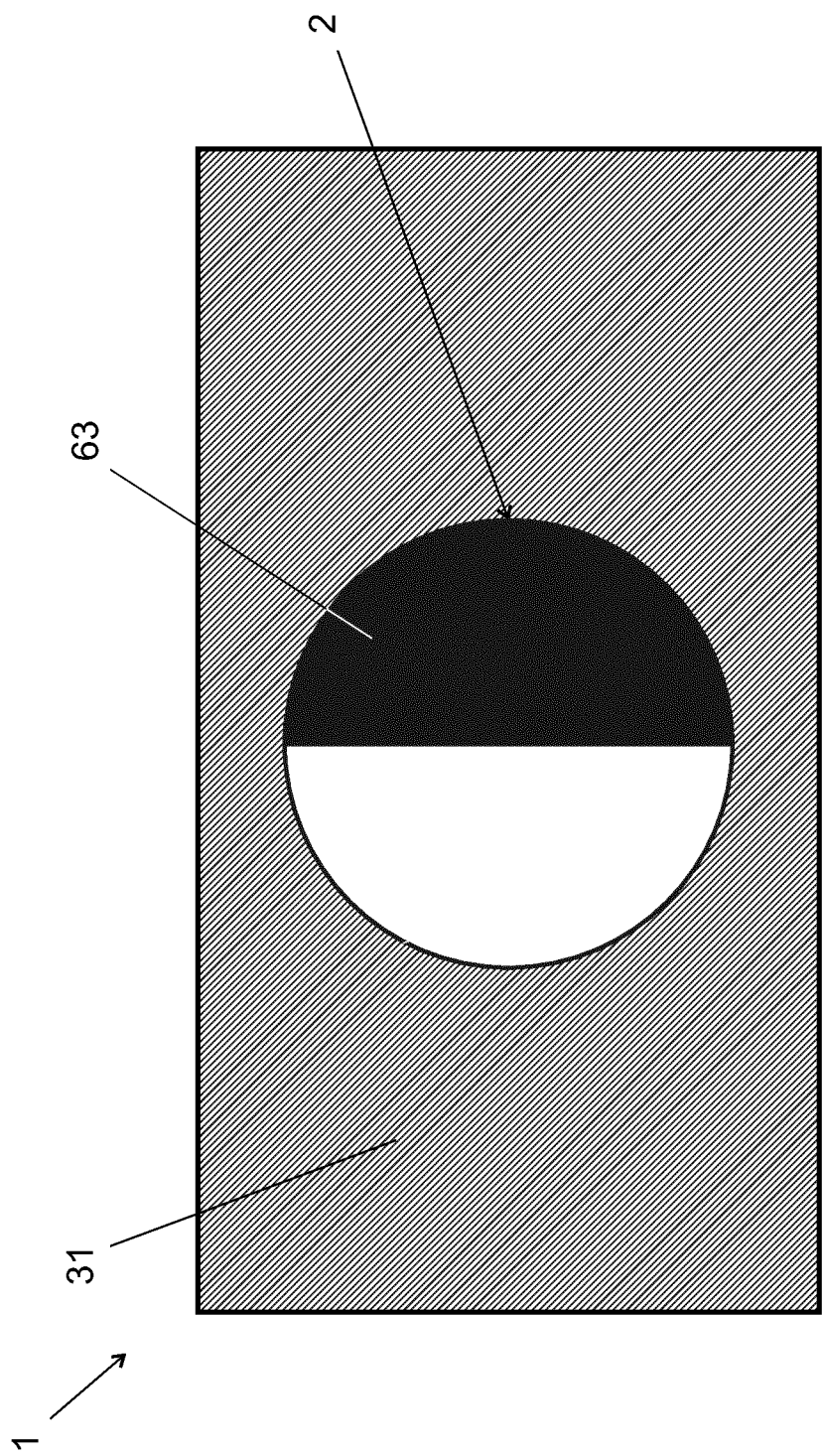

METHOD AND ARRANGEMENT FOR STERILIZATION AND STORAGE OF MEDICAL DEVICES

RELATED APPLICATIONS

This application is a national phase of PCT/EP2014/052367 filed on Feb. 6, 2014, which claims priority to CH-0408/13 filed on Feb. 6, 2013. The contents of those applications are hereby incorporated by reference.

FIELD OF THE INVENTION

The present invention concerns a method and an arrangement for sterilization and further storage of medical devices, in particular surgical instruments.

DESCRIPTION OF RELATED ART

In hospitals, medical instruments are generally sterilized by application of moist (steam) or dry heat, gamma-rays, chemical or plasma in a sterilization reactor, and stored in a plastic or crepe bag for storage and for a later transportation to the operating rooms.

Multiple-use medical devices are often sterilized according to following steps:

after operation plugging the device to decontaminate and sterilize for approximately 20 minutes in a container that contains decontaminant liquid for decontamination;

removing the device from the container, washing from such liquid and placing in a wash-machine for approximately 40 minutes;

drying;

conditioning the device with other medical devices as a set in a tray;

wrapping the whole set in the tray with multiple layers of crepe papers permeable to moist, and possibly in other packaging that could be sealed with a Tyvek sheet or similar sheet that allows penetration of heat, chemicals/etc;

placing into a sterilization reactor, for example a steam-based reactor; and after sterilization, unloading from the reactor and moved to a dedicated room waiting for a late usage.

Often, hospitals own a limited number of sterilization reactors that are usually large and expensive equipment commonly located in a dedicated room. As these machines normally require important amount of energy and deionized water, such machines operate on a predefined load of medical or surgical instruments with finite size. None of the devices could be removed before the entire reactor load had reach the selected Sterilization Assurance Level, or at least before this load has been maintained at a given temperature during a given time. Therefore, series of sterilizations have to be scheduled according to weekly/daily programs. After the sterilization cycle, sterilization products have to be evacuated outside the reactor and neutralized, for example by letting the medical devices cool down. The neutralization and removing procedure could last one hour or more, depending on the load and/or the reactor characteristics. Moreover, the putting into service of such reactors requires a parameters setting operation that is executed by specialized technicians.

This process is cumbersome and it may happen that a surgical operation needs to be rescheduled because some instruments are not ready and because it is not economical to sterilize only one or a limited number of devices. For example, if someone needs to sterilize a particular device at the end of the day, he cannot, since technicians would need to wait one more hour to unload the box at the end of the sterilization cycle.

There is therefore a need for a method and apparatus adapted for the sterilization of smaller loads, for example for single devices or sets with a limited number of devices.

There is also a need for a method and apparatus that can be used for sterilizing devices without any need for a technician to attend and to wait until the end of the sterilization cycle.

Moreover, medical instruments are to be packaged prior sterilization in order to avoid contamination after removing from the sterilization reactor. The sterile package is usually a multiple-layer crepe paper bag and/or a plastic bag sealed with Tyvek sheet which offers virtually no protection against shocks or hazards, and only limited protection against recontamination. Actually, crepe paper bag must remain dry to avoid contamination.

On the other hand, is it also known to use ozone for sterilization in various domains, for example for air purification, water processing, food processing or sterilization of medical devices.

For example, U.S. Pat. No. 8,048,370 (Barnes) discloses a method and an apparatus for purifying air, and suggests sterilization with ozone and ozonite by irradiating water vapour. Ozone could be destroyed by Ultraviolet UV-C irradiation.

US2003/0133832 (D'Ottone) discloses a method to disintox buildings, mail rooms, offices or other enclosed spaces after a contamination with nerve gases or anthrax.

WO2004/062800 (Potember and Bryden) discloses another method for neutralizing or destroying airborne pathogens, such as spores, bacteria and viruses, or chemical toxins in commercial air handling systems.

US2012/0056102 (Stanley) discloses a disinfection unit for disinfecting the entire surface of an item used in the food production chain. The disinfection box comprises a hollow, at least one ultraviolet light source within the hollow, reflective interiors for redirecting UV lights, an UV-transparent shelf for item holding and a unit door. This unit is relatively expensive, largely due to the price of the UV light source. As a consequence, this unit is poorly adapted to occasional use or for the storage of already sterilised items; the immobilisation cost of the unit is too high if it is not used regularly.

None of those documents suggests that the various methods described could be sufficient or even suitable for disinfecting medical devices, in particular surgical instruments.

Gordon discloses in US2009/0304553 a system dedicated to the sterilization of items contained in sealable packaging. The interior volume of the package is sterilized by ozone that will be generated by converting the oxygen present in the package by ultraviolet radiation. Gordon proposes to fabricate the items' pouch by a fabric constituted by quartz fiber and woven. Observing that the sterilization efficacy could be augmented by reacting ozone with water vapour, Gordon proposes to introduce water in vapour form in the package before sterilization. Mains drawbacks of this solution derive from the material used for the pouch. At first, the production cost of a quartz-fabric made pouch are elevate. Then, this type of non-rigid packaging is not adapted for object transportation as it could not offer any protection against shocks.

BRIEF SUMMARY OF THE INVENTION

It is therefore an aim of the present invention to provide a medical device, in particular surgical instrument, sterilization arrangement and method that alleviate or mitigate those drawbacks of the prior art.

In particular, it is an aim of the present invention to provide an arrangement for the sterilization of medical devices, in particular surgical instruments, whose costs are reduced, so that the sterilized devices or instruments can remain within the arrangement after sterilisation.

Another aim is to provide an arrangement for the sterilization and for storage of medical devices that offer a protection against shear stress, reducing the risk of contamination as well as to facilitate the transportation to the surgical theatre.

Another aim is to reduce the initial installation costs.

Another aim is to reduce the costs for each sterilization.

Another aim of this invention is to provide an ozone-based sterilization method and arrangement that could operate on a smaller load of medical devices, in particular surgical instruments, with various sizes.

Another aim of this invention is to provide an ozone-based sterilization method and arrangement that could be put into operation more rapidly than prior art sterilization reactors.

These aims are achieved by means of a method of sterilization of a medical device placed in a closable airtight container, comprising the following steps:
 a) placing said medical device inside a closable airtight container;
 b) closing said container;
 c) placing a Vacuum Ultraviolet Light source against a window of said container, wherein said window is transparent to Vacuum Ultraviolet light;
 d) irradiating a volume inside said container with Vacuum Ultraviolet Light through said window in order to generate ozone and/or ozonites within said volume;
 e) removing said Vacuum Ultraviolet Light source;
 f) waiting for an incubation time.

This method has the advantage that the UV light source is only used for a few minutes; after that, the container could be moved and the light source used with another reactor.

Tests have shown that the use of ozone and ozonites is very effective for the sterilisation of medical devices, surgical instruments, in particular instruments made of metal such as steel or plastic.

Moreover, the sterilisation costs associated with this method are much lower than with methods based on steam or chemicals. Moreover, ozone has the property to disintegrate by themselves, with a half-life period of about ten hours depending on temperature, material inside the container, material of the container, and so on. This avoids the problems which are sometimes caused by remaining traces of chemicals in chemicals-based sterilization methods.

The production cost of a container with an UV-transparent window could be very low. Since the Vacuum UV light source is independent from the container, and can be removed from the container after use, it is possible to use a single Vacuum UV light source for successively producing ozone and ozonites in a plurality of containers; the light source does not remain immobilized with the container during the sterilization cycle and until the medical devices are removed from the container.

Therefore, it is possible to use this container for the storage of the sterilised instruments until it is open in the surgical theatre in order to access and use the sterilised instruments. It is for example possible to sterilize a set of surgical instruments needed for a specific intervention in advance, to store the sterilised instruments within the container until the intervention, and to access the instruments at the very last moment. This avoids the risk of contamination due to packaging shear during sterilization or storage operations.

The Vacuum UV light source remains outside of the container and is placed against the window when in use. This reduces the production of ozone outside of the container. Against in this context means that the distance between the window and the light source is comprised between 0 and 5 cm during use.

The UV light source could be a UV lamp. Alternatively, the UV light source could be a UV laser. Alternatively, the UV light source could be the extremity of an optic fiber or other optic path that transports light from a remote light source, for example from a remote UV laser.

In order to further reduce the production of ozone outside of the container, this container can comprise a hollow including the window for housing the Vacuum UV light source during production of ozone. The Vacuum UV light source can thus be introduced into said hollow before use, and removed from this hollow after use. This hollow further reduces the production of ozone outside of the container.

The shape of the hollow may be adapted in order to allow a multidirectional Ultraviolet emission inside the container and/or a directly irradiation of a large volume inside the container.

The hollow may have a concave shape.

The ozone based sterilization reduces mechanical constraints on the container respect to other sterilization methods such as for example steam sterilization, since this ozone sterilizations could take place at atmospheric pressure.

The cost of the container is reduced, at first, by a scrupulous usage of UV-transparent material that is substantially limited to this the window.

The rest of the container could be made of different, for example cheaper and/or more resistant materials such as stainless steel, that are compliant with medical devices and/or surgical instruments storage and sterilization constraints, without any restriction to UV-transparent/semi-transparent materials.

The container could comprise a seal between a lid and a tray, to prevent ozone from escaping the container or contaminants to enter into the container.

The UV transparent window could be made, without limitation, of quartz, $MgF_2$, $CaF_2$, $Al_2O_3$, SiC, LiF, NaF, NaCl, KCl, KCl, $SrF_2$, RbCl, $Y_3Al_5O_{12}$, $BaF_2$, $ZrO_2$ or CsI. RbBr, KBr or $LaF_3$ could be used although these materials are less transparent to vacuum ultraviolet light.

In one preferred embodiment, the method further comprises the following steps after the incubation:
 g) placing a UVC or Middle Ultraviolet Light source against such window;
 h) irradiating such volume inside said container with UVC or Middle Ultraviolet Light through the window in order to destroy ozone and/or ozonites;
 i) removing the UVC or Middle Ultraviolet Light source.

As, without ozone destroying operation, the reach of a safe-level of ozone within the container could require up to some days, such operation permits a rapid use of so sterilized medical devices.

Therefore, the UVC or Middle Ultraviolet Light source can be used for destroying ozone successively in a plurality of containers.

This embodiment further permits to circumscribe an escape of reflected Ultraviolet light emission outside the container.

The hollow may have an opening for the introduction of the light source, with a shape and dimension adapted for the easy introduction of the light source with little possibility for ozone created in the hollow to escape.

In one preferred embodiment, the hollow in one side of the container is closed by the introduction of the Vacuum Ultraviolet Light source into such hollow.

This embodiment permits to confine an expansion of ozone/ozonites outside the container, wherein such ozone/ozonites are created by the step of irradiating the volume inside the container with Vacuum Ultraviolet Light.

In one embodiment, the method further comprises an additional step of j) placing or filling a water tank inside the container before the step of closing the container.

The placing or filling of a water tank inside the container ensures a high relative humidity ("RH"), allowing a creation of ozonites by reacting ozone with water vapour inside the container. The creation of ozonites further increases the sterilization efficacy of the method of sterilization. The water tank could be a plate water tank that comprises means for retaining water and adapted to provide two opposite surfaces of contact between the inside contained water and a volume inside the container.

In one embodiment, the method further comprises an additional step of k) placing a desiccant element or unit inside the container before the step of closing the container.

In one embodiment, the method further comprises a step of l) applying vacuum or replacing oxygen by another gas in such hollow, in order to limit the excessive formation of ozone outside of the container.

In one embodiment, the method further comprises a step of m) measurement of ozone/ozonites concentration inside said container.

In one preferred embodiment, the method of sterilization comprises the repetition of the steps of:

a) placing medical devices inside a particular closable airtight container;

b) closing the container;

c) placing a Vacuum Ultraviolet Light source against the window of the container;

d) irradiating the volume inside the container with Vacuum Ultraviolet Light through the window;

e) removing the Vacuum Ultraviolet Light source;

f) waiting for the incubation time;

within the same container; wherein such container is reusable.

The invention further relates to an arrangement comprising a closable airtight container for storage and sterilization of inside contained medical devices, said container comprising:

an airtight closure for the introduction of said medical devices into said container and removal of sterilized said medical devices from said container; and a window transparent to Vacuum Ultraviolet light; wherein said window extends over an outside surface of said container that is tiny respect to the outside entire surface of said container;

whereas the rest of said container substantially consists of an Ultraviolet non-transparent material. In an embodiment, said window extends over an outside surface of said container that is smaller than 25 percent of the outside entire surface of said container.

In a preferred embodiment, the outside surface of the window is less than 10 percent of the outside entire of said the entire container.

In one embodiment, the arrangement comprising a closable airtight container for storage and sterilization of inside contained medical devices, said container comprising:

an airtight closure adapted to introduce such medical devices into the container and adapted to remove the medical devices from the container; and a hollow with a window transparent to Vacuum Ultraviolet light and to UVC and/or Middle Ultraviolet light; wherein such hollow adapted to at least partially surround a UV light source; whereas the rest of such container substantially consists of an ultraviolet non-transparent material.

In one embodiment, the container is substantially made of stainless steel.

This embodiment provides a container that is particular adapted to be reused for successive sterilizations of medical devices, in particular surgical instruments, within the same container.

This embodiment further provides a container that does not generate toxic compounds that remain at the end of the sterilization cycle.

In one embodiment, the container further comprises a water tank located inside such container. The water tank could provide two opposite surfaces of contact between the water and air inside the container.

In one embodiment, the container further comprises a desiccant element or unit located inside such container.

This embodiment permits to control humidity inside the container after the sterilization process, especially during storage times of inside contained objects.

In one embodiment, such hollow of the container comprises a concave part with at least one UV-transparent side.

In one preferred embodiment, the hollow of the container is substantially cylindrical, conical or tubular.

In an embodiment, the hollow further comprises a frame for holding the window.

In one embodiment, the container further comprises a mirror adapted to reflect back ultraviolet light through the window.

In one embodiment, the arrangement comprises a lens for compensating for deviation of UV light at the interface between air and the window.

In one preferred embodiment, the arrangement further comprises a Vacuum Ultraviolet Light source adapted for removable insertion within the hollow.

In one preferred embodiment, the arrangement further comprises a Middle Ultraviolet Light source adapted for removable insertion within the hollow.

In one preferred embodiment, the Vacuum Ultraviolet Light source or the Middle Ultraviolet Light source comprises a fixation adapted to releasable fix it to the container in order to build an airtight closed volume between such light source and the window.

In an embodiment, the arrangement further comprises a gas source for replacing oxygen by another gas in such airtight closed volume.

In one embodiment, the arrangement further comprises a computer-operated processing unit adapted to trigger and control execution of the following steps of the method of sterilization:

d) irradiating the volume inside the container with Vacuum Ultraviolet Light through the window;

f) waiting for the incubation time; and h) irradiating the volume inside said container with UVC or Middle Ultraviolet Light through the window.

BRIEF DESCRIPTION OF THE DRAWINGS

The invention will be better understood with the aid of the description of an embodiment given by way of example and illustrated by the figures, in which:

FIGS. 13-15 show a housing provided with a pivoting shutter.

DETAILED DESCRIPTION OF POSSIBLE EMBODIMENTS OF THE INVENTION

Figure 1:
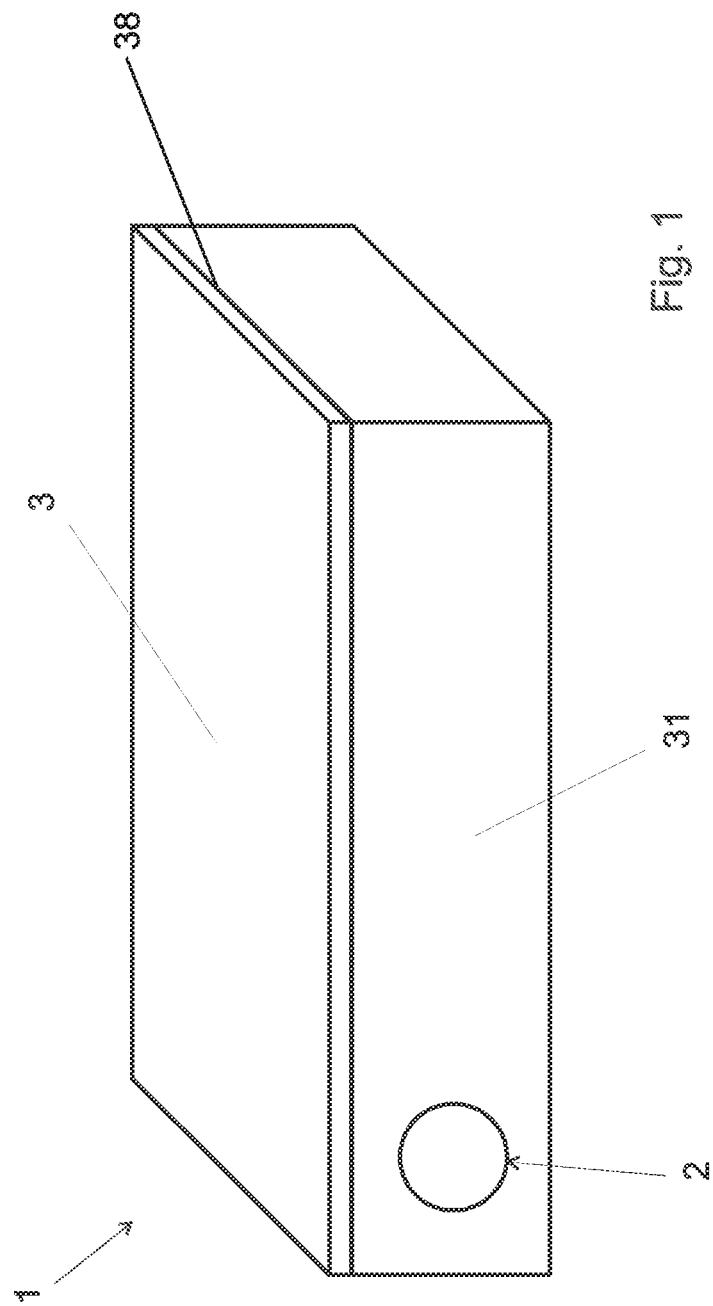
FIGS. 1 to 4 show a first embodiment of a container according to the invention.
Figure 2:
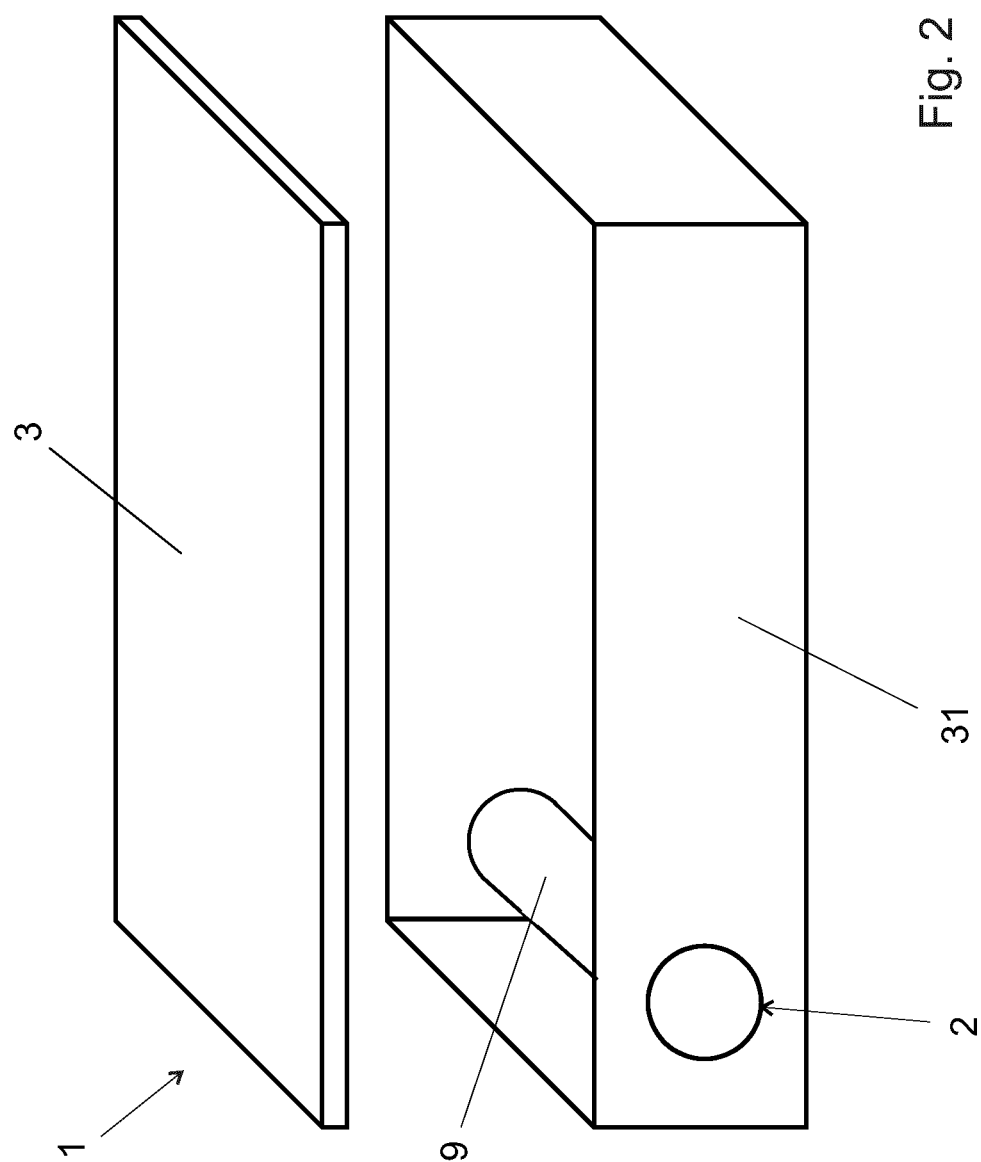
Figure 3:
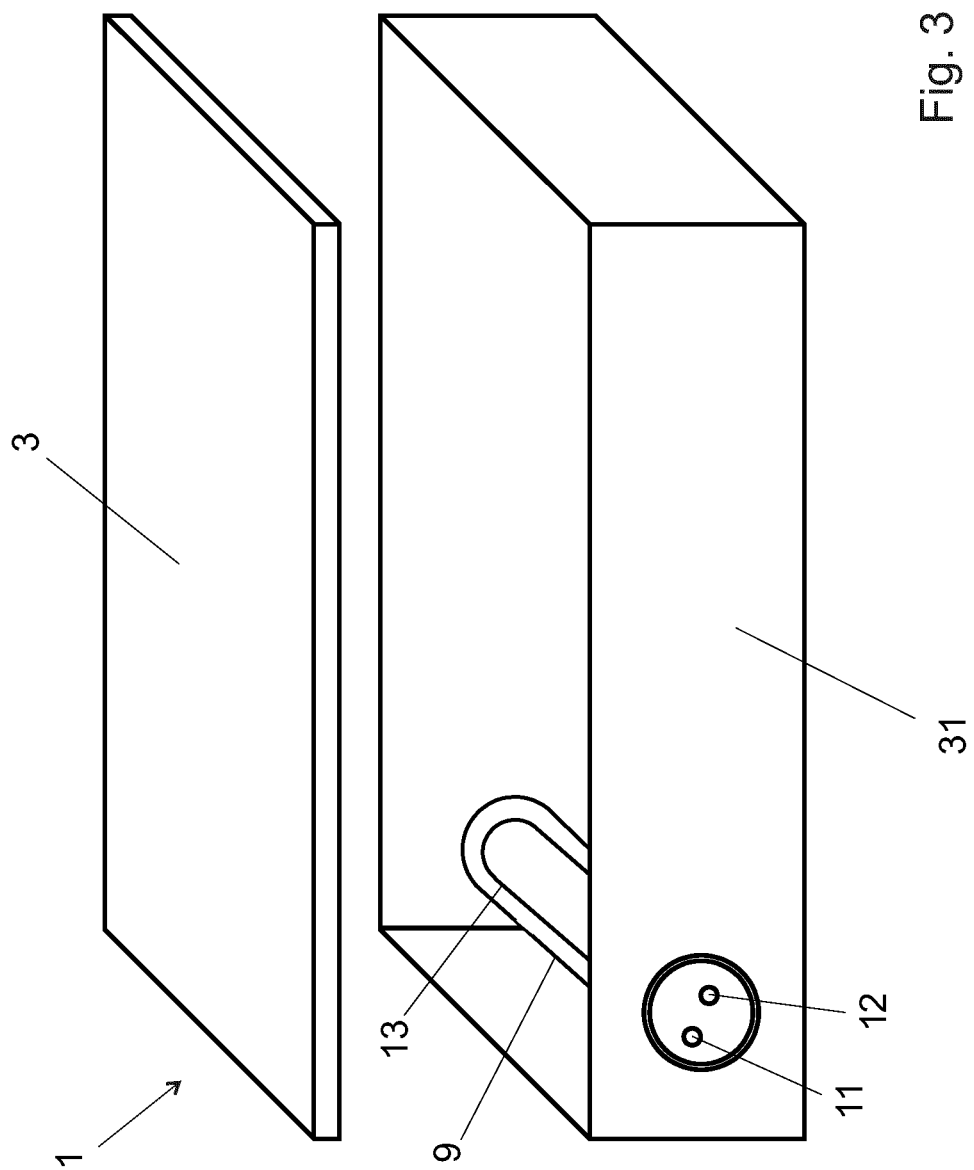

The invention refers to a method and an arrangement for sterilization and storage of medical devices, in particular surgical instruments.

FIGS. 1-4 show an arrangement comprising a closable airtight container 1 according to the invention. This container comprises a hollow 2, a tray 31 and a lid 3. The hollow 2 comprises a window 9, here a cylindrical window that is transparent to UV light, in particular transparent to Vacuum Ultraviolet light and to UVC and/or Middle Ultraviolet light. The rest of the container could be made of metal and/or any other convenient material, e.g. a cheaper material, that is compliant with medical devices or surgical instruments sterilization and storage constraints, without any restriction to UV-transparent/semi-transparent materials. The lid 3 is removable from the tray 31 in order to give access to the stored objects. Alternatively, the lid 3 could be integral with the tray 31, while an object may be inserted in the container through an airtight closure 38 adapted to introduce and to remove surgical instruments to/from the container 1.

According to the invention, the container is adapted for medical device storage and sterilization, in the sense that it meets regulatory requirement for sterilization and storage of medical devices, in particular for sterilization and storage of surgical instruments inside or near a surgical theatre.

The closable airtight container according to the invention could be any kind of container adapted to be closed impeding the passage of air and other contaminant in or out the container, like box containers and closable trolleys. According to the invention, the shape and the volume of the container is adapted to medical devices, in particular surgical instruments, preferably offering a volume from few litres up to few hectolitres.

Medical devices in the sense of the invention are all kind of portable surgical objects, instruments, tools, equipment as well as portable medical devices made of metal and/or plastic and active medical devices with embedded electronics.

Hollow in the sense of the invention could comprise any kind of concave, hollow portion, for example a cylindrical, pyramidal-shaped and/or tubular-shaped portion, adapted to at least partially surround an UV lamp.

Window in the sense of invention could be any kind of opening in the container or hollow adapted to allow the passage of visible and UV irradiations while preventing the passage of contaminants. The window could comprise any kind of flat, convex and/or concave UV-transparent material bodies with rectangular, rounded or any other shapes. The window could comprise cylindrical, pyramidal-shaped, tubular-shaped UV-transparent material bodies.

The window 9 could be made of quartz or any other convenient material, for example $MgF_2$, $CaF_2$ or $Al_2O_3$ that are highly transparent to both Vacuum Ultraviolet and Middle Ultraviolet lights.

In order to better control generation and destruction of ozone and/or ozonites inside the container during sterilization steps as well as to avoid ozone generation outside the container during these steps, the lid 3 and the tray 31 could comprise an UV non-transparent material. Advantageously, the lid 3 and the tray 31 could be made of an UVC non-transparent material.

The hollow 2 of FIGS. 1-4 is defined by an opening in one side of the container and by a window 9 whose transparent cylindrical part 92 is extending inwards the container 1. The form and the size of this hollow 2 are adapted to permit an insertion of an irradiating part 13 of an UV light lamp 10. This hollow permits, in cooperation with an UV light source, to increase the surface of the window 9 and/or to directly irradiate a larger volume inside the container. In order to allow a substantially complete insertion of an irradiating part of an UV light source, the window 9 could have and/or comprise elements having substantially cylindrical-shape, substantially conical-shaped and/or a substantially tubular shape.

Figure 4:
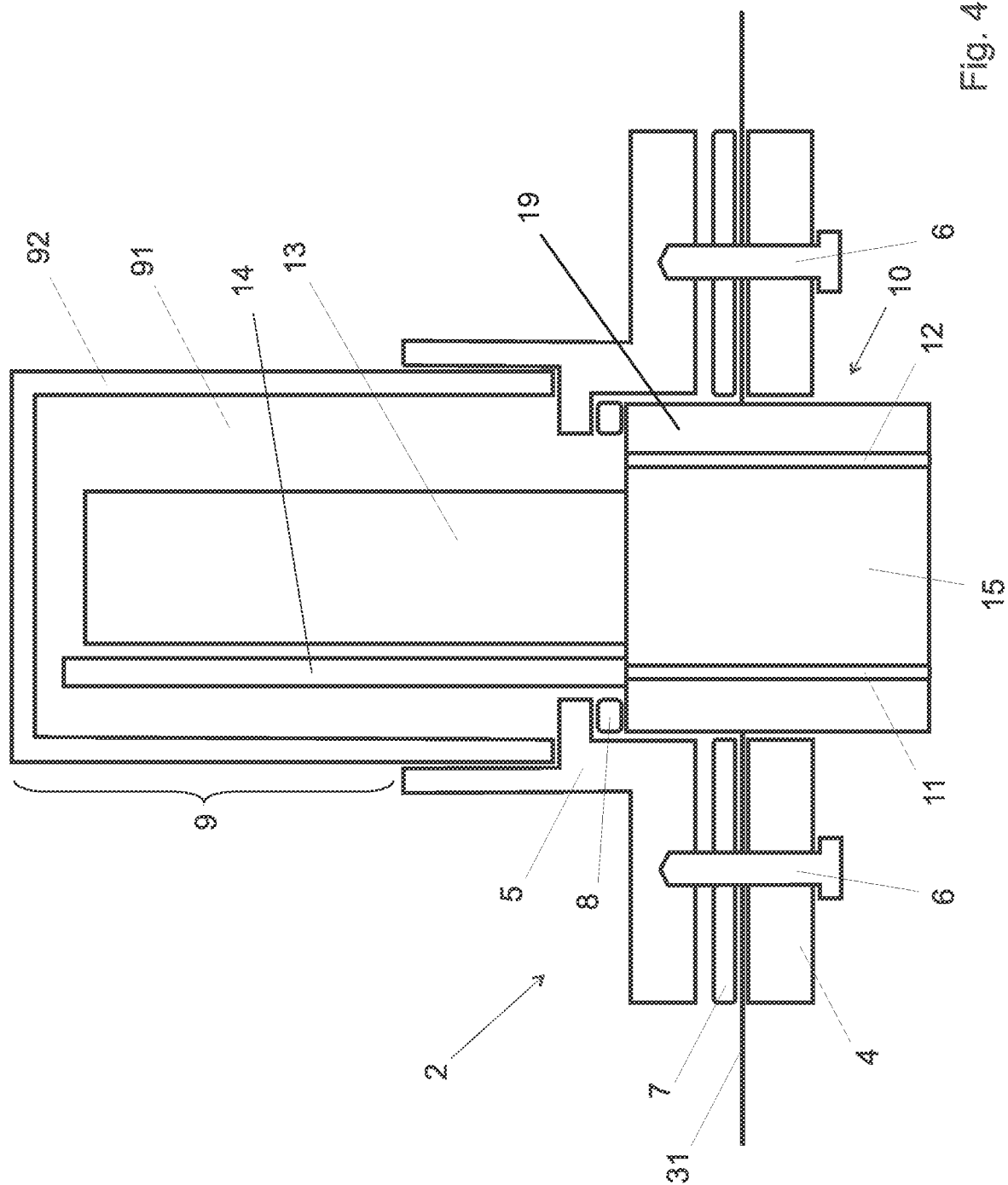

The window 9 could be supported by a window frame, such as for example a stainless steel window frame, as illustrated in FIG. 4. In this example the window frame comprises an external frame part 4 and an internal frame part 5 that fix the hollow 2 to the tray 31 by screws 6. A seal 7 is mounted between the internal frame part 5 and the tray 31 for preventing water, air, nitrogen or ozone from flowing inside and/or outside the container 1 through the window frame.

An additional seal 8 could be mounted on a surface of the internal frame 5 that is dedicated to support the UV light lamp 10. This seal 8 prevents water, air, nitrogen or ozone from flowing inside and/or outside a volume 91 that is formed by the insertion of the irradiation part 13 of the UV lamp 10 inside the hollow 2.

Furthermore, this volume 91 between the irradiation part 13 of lamp 10 and the window 9 could be flushed with nitrogen gas or other VUV inert gas to reduce oxygen concentration between the lamp and the window 9, and thus the generation of ozone outside the container. A support 15 of the lamp 10 could be provided with a first hole 11 cooperating with a tube 14 in order to flush gas into such volume while a second hole 12 of the support 15 guarantees the taking over of such gas. Alternatively, a vacuum could be created between the window and the light source.

The hollow 2 of the FIG. 4 could be advantageously comprised in a tray of a closable trolley for surgical instruments. The inside contained instruments could be sterilized and stored inside the same trolley inside or near the operating theatre.

In FIGS. 1-4 the hollow 2 opens in one side of the tray 31. In other embodiments, the hollow 2 could open in the lid 3 or in other parts of the container where available.

Figure 5:
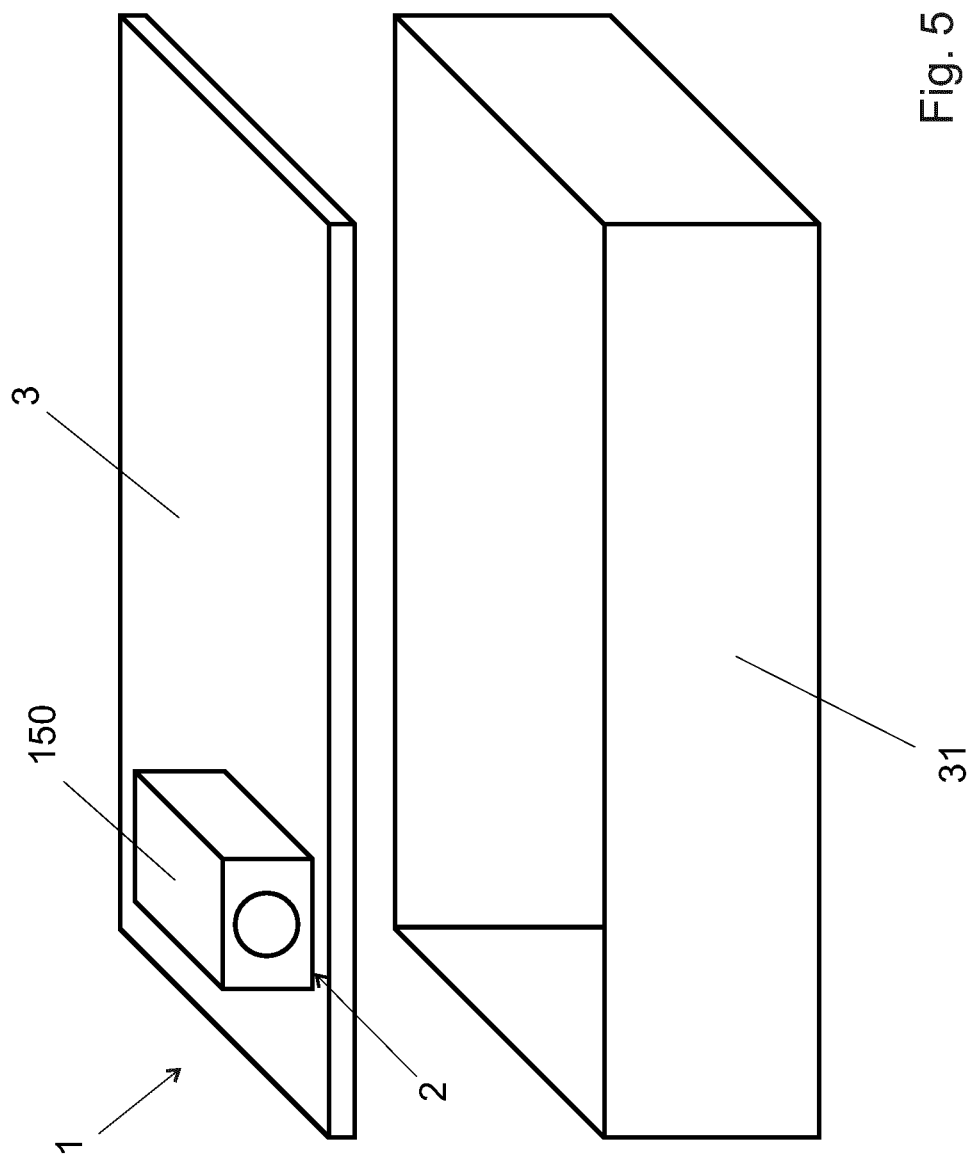
FIG. 5 shows a second embodiment of a container according to the invention, wherein the hollow is placed in a lid.

In FIG. 5, the hollow 2 is defined within a dedicated box 150 that is fixed to external surface of the lid 3. A wall of this box 150 comprises an UV-transparent window 9, advantageously in form of an UV-transparent plate. The box will be positioned on the lid 3 so that the UV-transparent window overlaps a dedicated overture of the lid 3.

Figure 6:
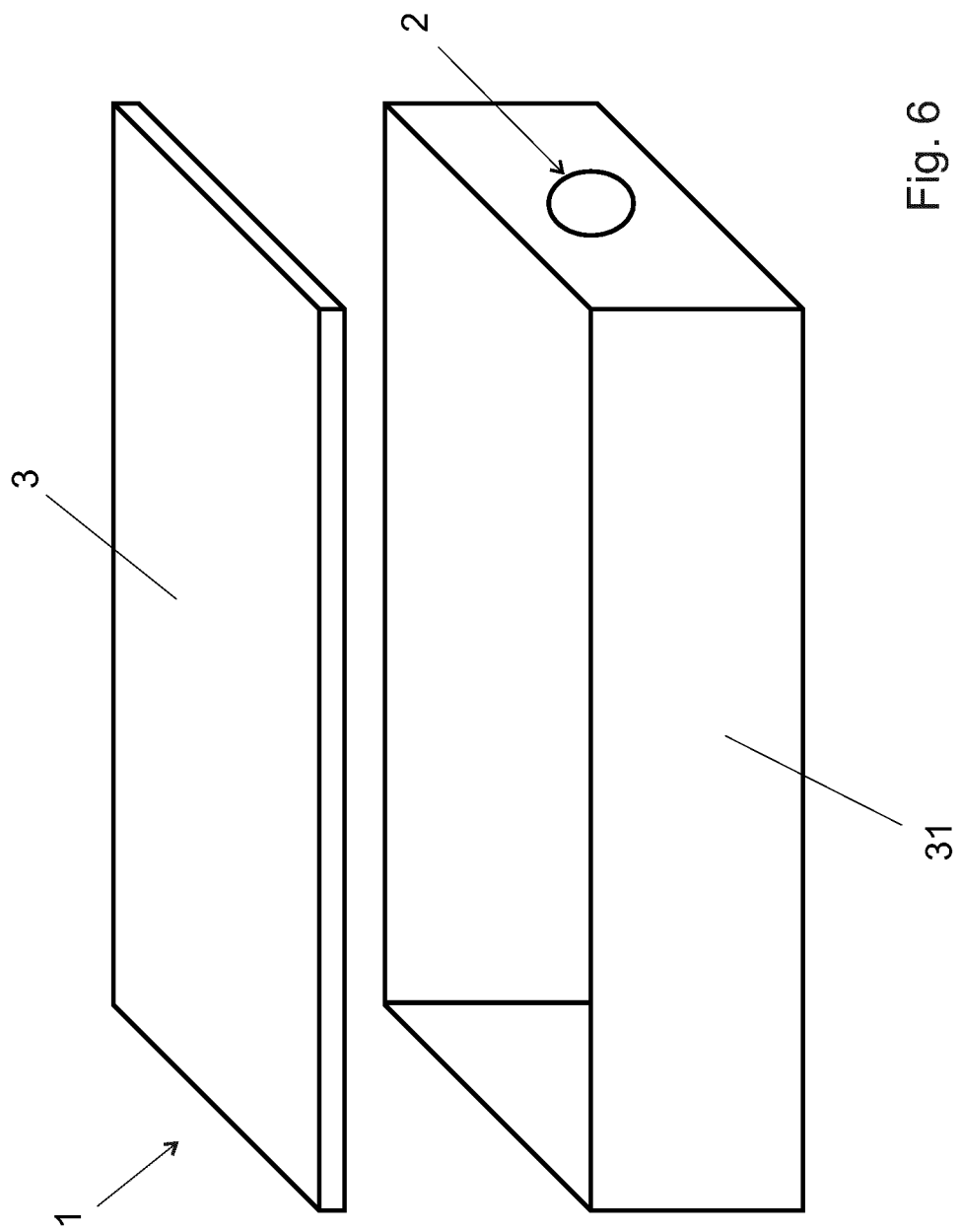
FIGS. 6-7 show a third embodiment of a container according to the invention, wherein the UV-transparent part of the window is flat.
Figure 7:
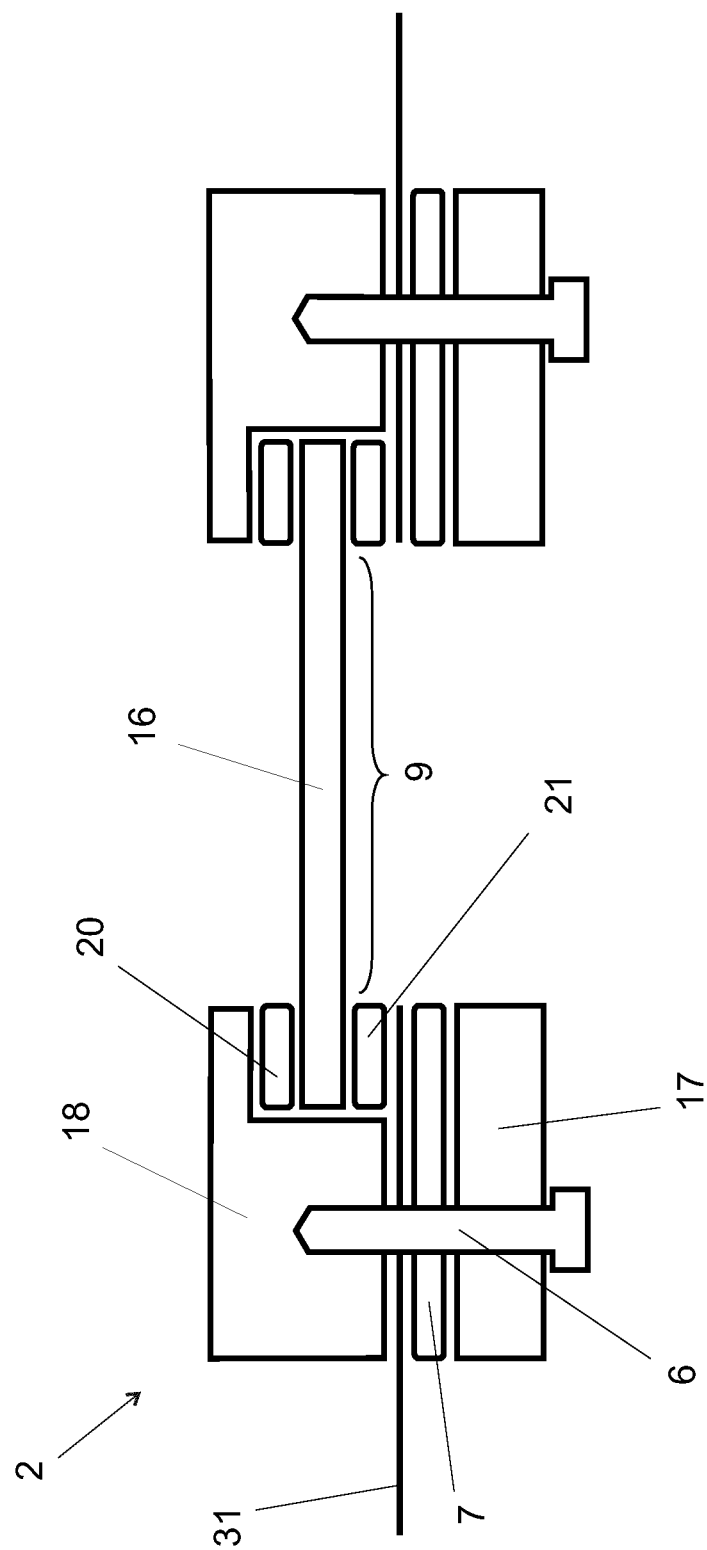

FIGS. 6 and 7 illustrate an embodiment wherein the hollow 2 is defined by the frame of a window 9 constituted by a UV-transparent plate 16. The window is flat, but could be slightly concave or convex, or plano-concave. This embodiment is well adapted for mono-directional UV light sources, such as UV laser sources or extremities of optic fibers that spread light only in one direction. In this case, the window could act as a lens that diverges the laser beam in order to raise the volume within the container where it interacts with air. Alternatively, or in addition, an additional diverging lens could be used between the light source and the window, or within the container.

In a similar way, the ozone destruction could be achieved with a UVC or Middle Ultraviolet Laser.

An UV laser source has the advantage over UV lamps to avoid any manipulation of the lamp; the laser, or the optic fiber, can be plugged to the frame, or maintained at distance of the window, without any need to touch the light source.

Additionally, the use of a laser permits to reduce the surface of the transparent window 9 to a tiny surface. For example, a less than 20 mm diameter window, for example a 9 mm diameter window 9, could be used in cooperation with a UV laser.

The laser could be located at a remote distance and the UV rays could be directed to the window 9 by one or a plurality of optic fibers, or through another light path that reduces the generation of ozone in air.

Figure 11:
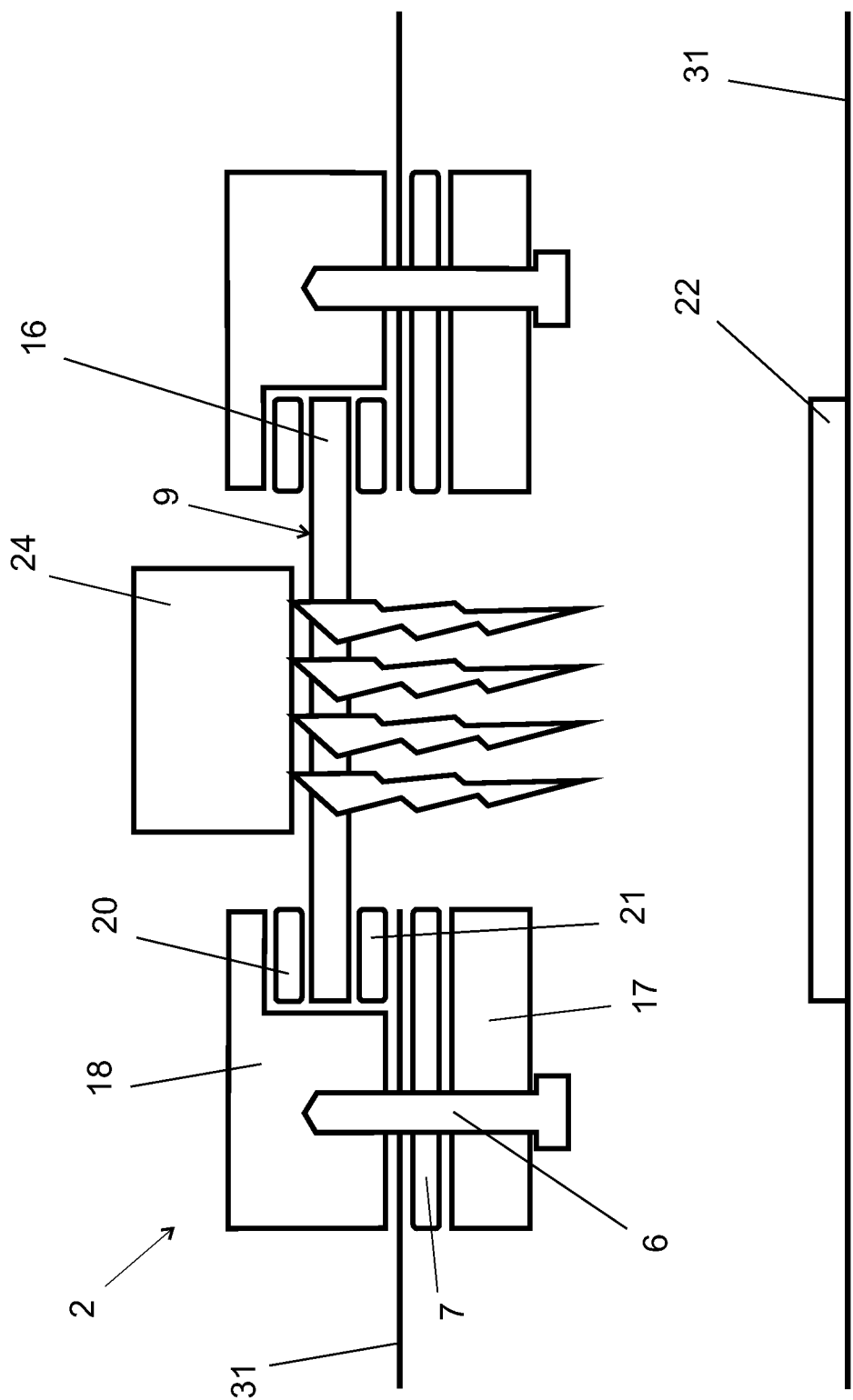
FIGS. 11 and 12 show an ozone concentration measurement system.

The window frame supports the window and could be for example a stainless steel window frame. In this example the frame comprises an internal frame part 17 and an external frame part 18 defining the hollow 2 and fixed to the tray 31 by screws 6. The window frame could also be part of the tray. The shape of the external frame part 18 form the hollow 2 that substantially surround an emitting surface of a UV light source, as shown in FIG. 11, in order to avoid or at least to mitigate an outwards direct emission and/or an outwards reflection of UV light on an external surface of the container or of the window.

A plurality of seals 7, 20, 21 is used for preventing water, air, nitrogen or ozone from flowing inside and/or outside the container 1 through the hollow 2.

Holding means (not represented) may be provided in the container 1 for holding the contained objects and preventing it from being moved sterilization and storage operations. Those holding means may further been arranged for preventing UV lights entering into the container for reaching damageable parts of the objects, for example UV-sensitive parts if the objects in the container have some UV sensitive parts.

Advantageously, the container could be equipped with at least one water tank. The role of said tank(s) is to maintain high relative humidity (RH) inside the container to permits an optimal creation of ozonites by UV light irradiation. A 100% RH is an advantageous situation for said sterilization process.

The water tank could be placed and designed in order to retain water from flowing within the container by gravity force, thank to water surface tension. For example, cavities or hollows could be placed on the internal, bottom part of the tray and/or in other parts of the container.

The water tank could contain means for retaining water inside the tank, such as a sponge, foam or other water retaining means for preventing water from flowing within the container. Alternatively, the water tank could be covered by a waterproof, breathable fabric such as Gore-Tex®.

Figure 8:
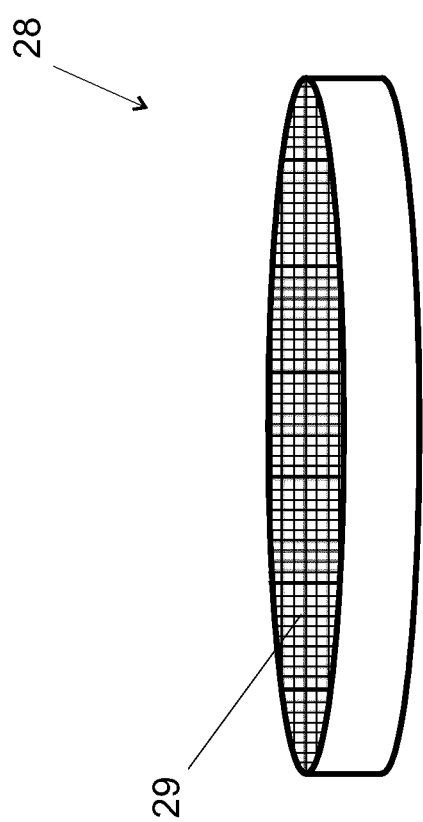
FIG. 8 shows a grid-shaped water tank.

In case of a water tank 28 comprising or consisting of a grid 29, water can be retained by superficial forces against the grid, thus preventing a fast flow of water exiting the tank, as illustrated by FIG. 8.

The water tank could be a disk-shaped tank provided with water retaining means, for example with sponge, placed substantially vertically in the container in order to provide two surfaces of contact between the water and the volume inside the container.

Figure 9:
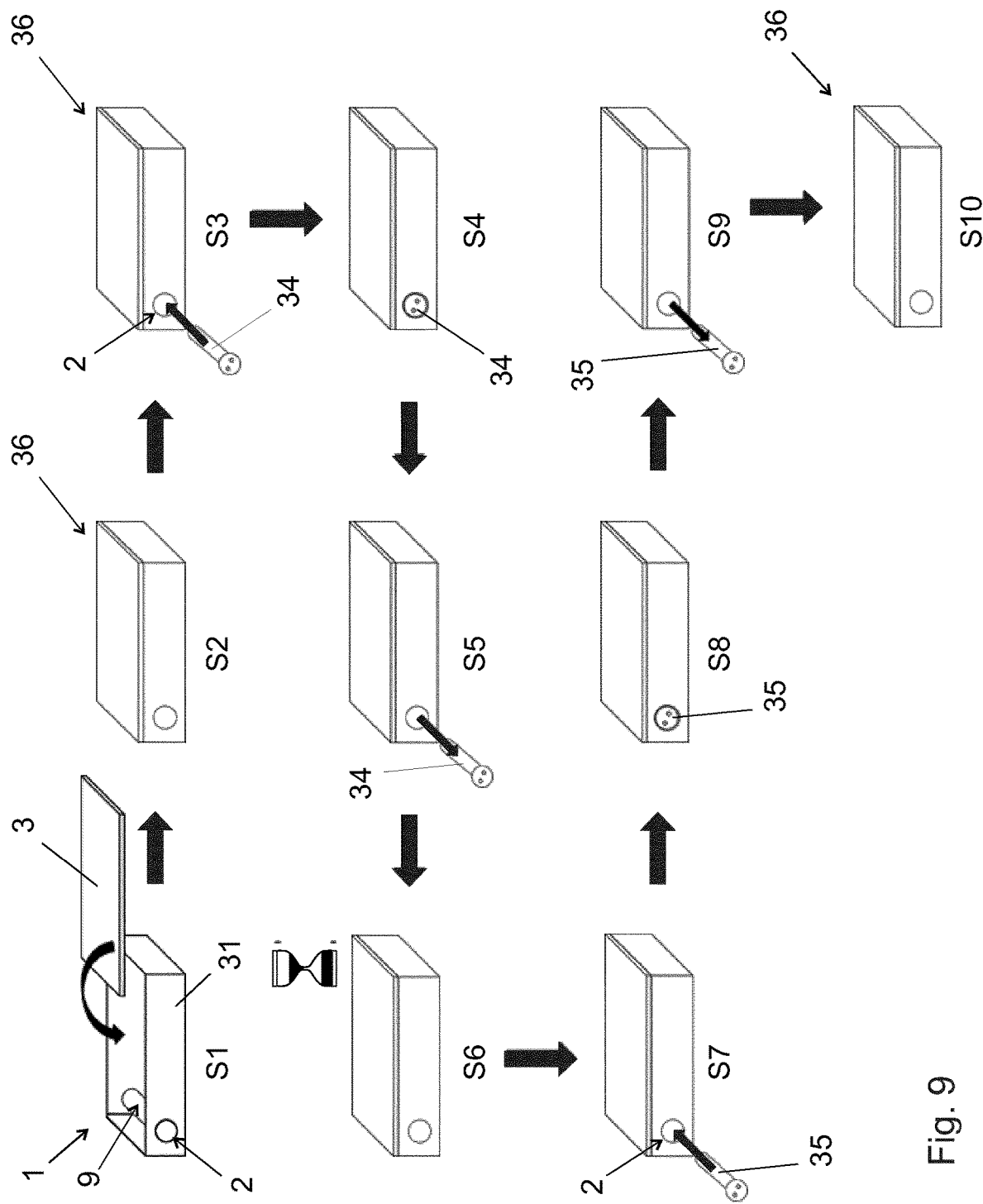
FIG. 9 shows a graphical representation of a sterilization process according to the invention.

FIG. 9 shows a graphical representation of a sterilization and storage process according to the invention. In this embodiment, the method of sterilization and storage of medical devices, in particular surgical instruments, placed in said container consists in 10 steps (S1-S10).

In the first steps S1, a medical device or devices to sterilize and a water tank (not shown) are placed in the tray 31 of the container 1. A desiccant unit or element could be placed in the tray 31.

Additionally, a sterilization indicator, such as a rubber with bands that will change color during the sterilization, could be placed at a convenient place inside the container, to be visible through the window. This indicator could be checked at the moment of the container overture in surgery theatre in order to verify the sterilization status of contained medical devices.

In order to eliminate rest of water that remains in the container after the sterilization procedure, the quantity of water initially retained in the water tank is adapted to such procedure. A computer-operated processing unit could be used to determine such quantity, depending on the shape and the volume of such container and the number and type of contained medical devices. This information could be furnished and managed through an identification label provided on an external or internal surface of the container, e.g a code bar label or RFID tag.

The container is then closed and/or sealed, by example by placing a lid 3 on the tray 31 (S2). If the closable container is a trolley, such container could be airtight closed and/or sealed, by example, by closing all the drawers of such trolley.

An irradiating part of a Vacuum Ultraviolet light source 34 is then placed in a hollow 2 comprising a UV-transparent window 9 of the closed/sealed container 36 (S3). Alternatively, a Vacuum Ultraviolet light source 34 could be placed near the hollow 2 having a hollow that is adapted to substantially surround an emitting surface of the Vacuum Ultraviolet light source 34.

This source irradiates the content of the container through the UV-transparent window 9 of the hollow 2 of the container in order to generate ozone and/or ozonites within said volume (step S4). According to literature, ozone could be created by UV ray with wavelength shorter than 200 nm. In an embodiment, the wavelength of the said light source could be comprised in a range from 130 nm to 200 nm.

A computer-operated processing unit could be employed to trigger and control the execution of this step of irradiating the content of the container through the UV-transparent window 9.

Depending substantially on the size and the shape of the container as well as on the sizes, the shapes and the disposition of the inside contained objects, the hollow 2 could be located in the tray or in other parts of the container so that the irradiation of the Vacuum Ultraviolet light source could generate ozone inside the container in an effective and efficient way. Preferably, the window 9 of the hollow 2 is located on the container so that the Vacuum Ultraviolet light source could irradiate inside the closed container for a distance of at least 10 cm.

The hollow 2 could be located in the tray or in other parts of the container in order to directly irradiate a larger volume inside the container.

During this step, oxygen concentration between the Vacuum Ultraviolet light source and the window 9 could be reduced by creating locally a vacuum situation. For example, suction caps and/or air pumps could be employed. Alternatively, oxygen could be replaced by another gas, in order to limit the excessive formation of ozone outside of said container.

After such irradiation step, the Vacuum Ultraviolet light source 34 is then removed from such hollow 2 of the container (S5).

During the incubation time (S6), ozone and ozonites in the tray sterilize the inner content of the tray. The incubation time is defined according to the selected Sterilization Assurance Level (SAL). The inside contained object, the number of objects as well as its sizes, shapes and material condition such incubation time. This step may last for several hours.

A computer-operated processing unit could be employed to trigger and control the execution of this step of waiting for such incubation time. Such incubation time could be managed through an identification label provided on an external surface of the container, e.g. like a code bar label or RFID label.

In case the use of the sterilized surgical instruments is planned for a later period that overcome the degradation period of the residual ozone/ozonites, the container 1 could be immediately stored after removing the Vacuum Ultraviolet light source (S5) without further operations.

In case an urgent or a quickly use of the sterilized instruments is requires or desired, an irradiating part of an UVC or Middle Ultraviolet light source 35 is then placed in or near the hollow 2 of the closed/sealed container 36 (S7), after waiting for the incubation time.

This source 35 irradiates the volume inside the sealed container through the window 9 in order to destroy ozone and/or ozonites (step S8). Tests have shown that ozone is efficiently destroyed by UV rays with wavelengths from 220 nm up to 290 nm. In a convenient way, the wavelength of the said light source could be comprised in a range from 240 nm to 280 nm. Low pressure Hg lamps could be used, as said lamps emit 254 nm UV-ray.

A computer-operated processing unit could be employed to trigger and control the execution of this step ozone and/or ozonites destruction. An identification label provided on an external surface of the container could provide the required information for this task.

After such UVC or Middle Ultraviolet light irradiation step, the irradiating part of the UVC or Middle Ultraviolet light source 35 is then removed from such hollow 2 (S9).

The object or objects placed in said sealed container 36 are safely sterilized and ready for use and/or for storage within the container without further packaging procedures (S10). Furthermore, this object or these objects could be further transported or exported in a sterile manner, within the same container used during the sterilization cycle.

Alternatively, a use of a UV light source adapted to selectively irradiate Vacuum Ultraviolet light and UVC or Middle Ultraviolet light could replace the use of two UV light sources 34 and 35. In this case, this UV light source could be placed inside or near the hollow 2 once at step S3 and removed in step S9.

Figure 10:
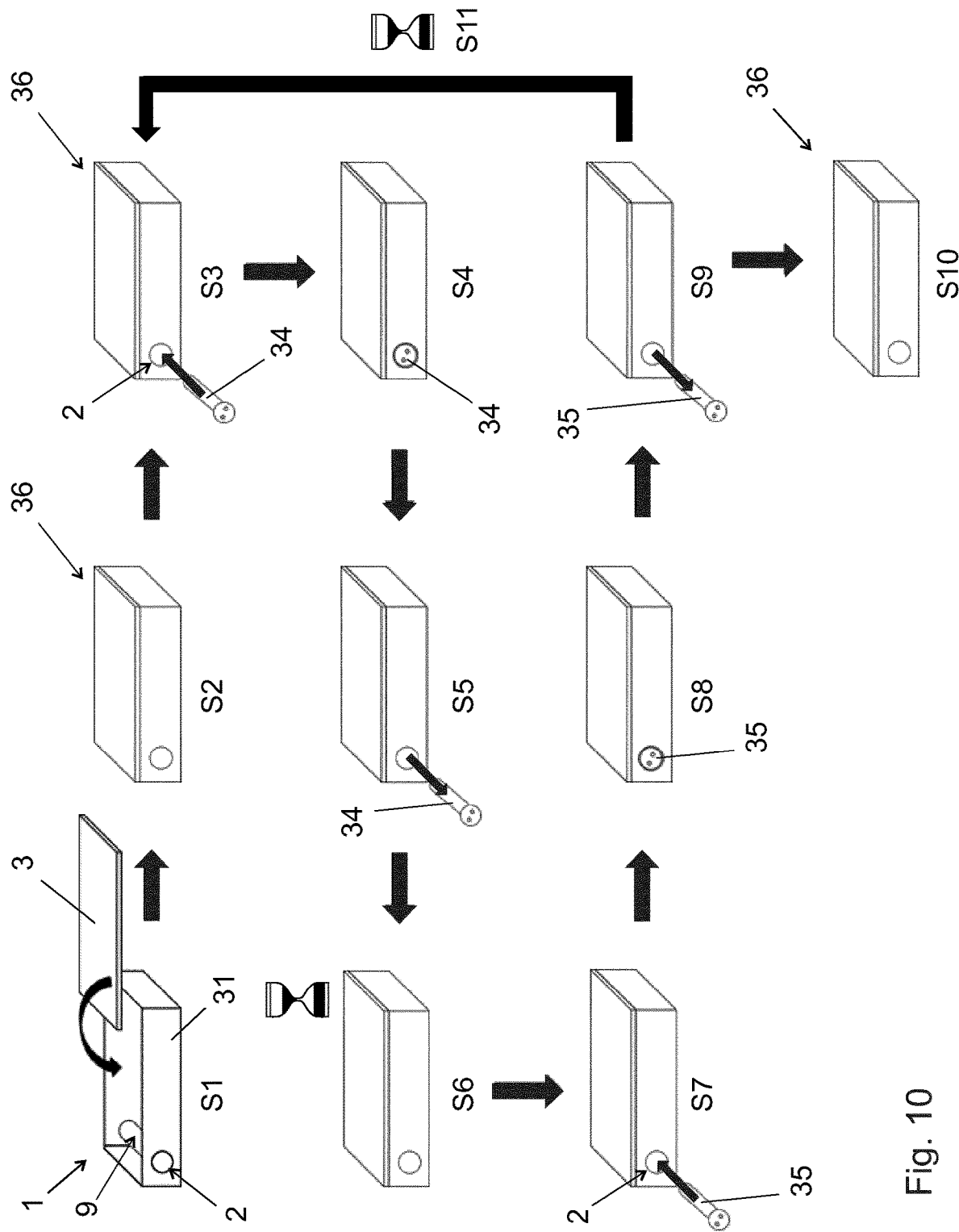
FIG. 10 shows another graphical representation of a second embodiment of a sterilization process according to the invention.

FIG. 10 shows a graphical representation of another sterilization process that involves a repetition of ozone and/or ozonite generation, ozone and/or ozonite destruction steps and incubation steps.

This sterilisation process involves at least a repetition of the steps of:

irradiating the volume inside the sealed container (36) with Vacuum Ultraviolet Light through such window 9 of the hollow 2 of the sealed/closed container 36 in order to generate ozone and/or ozonites within said volume (S3-S4-S5);

waiting for an incubation time (S6);

irradiating the volume inside the sealed/closed container with UVC or Middle Ultraviolet Light through such window 9 in order to destroy ozone and/or ozonites (S7-S8-S9).

Each repetition is preceded by a step of waiting for an incubation time (S11) that will be executed after the step of irradiation with UVC or Middle Ultraviolet light (S7-S8-S9).

This sterilization procedure could involve a repetition of the insertion of an irradiation part of a Vacuum Ultraviolet light 34 in the hollow 2 (S3) and the successive removing (S5).

This sterilization procedure could involve a repetition of the insertion of an irradiation part of a UVC or Middle Ultraviolet light 35 in the hollow 2 (S7) and the successive removing (S9).

Alternatively, an UV light source adapted to selectively irradiate Vacuum Ultraviolet light and UVC or Middle Ultraviolet light could be inserted once inside the hollow at the first execution of the step S3 and removed at the last execution of the step S9.

Knowing that the time required generating ozone inside containers is very short with respect to the incubation time, the above-mentioned procedures allow a rapid reuse of the UV light sources 34, 35 for other procedures. These procedures permit a pipeline-approach of a plurality of parallel sterilization procedures implying the same UV light sources and a plurality of containers of the invention.

In an embodiment, the method of sterilization further comprises an additional step of placing a desiccant inside said container before to seal said container. A desiccant, like silica gel, could be placed inside the container in order to control humidity after the sterilization process. The desiccant is selected so that the desiccating dynamic inside the container doesn't interfere with the humidity distribution and homogeneity provided by the water tank during the sterilization process.

Ozone measurement system could be used to measure ozone quantities or densities in containers and/or in the sterilization equipment.

Figure 12:
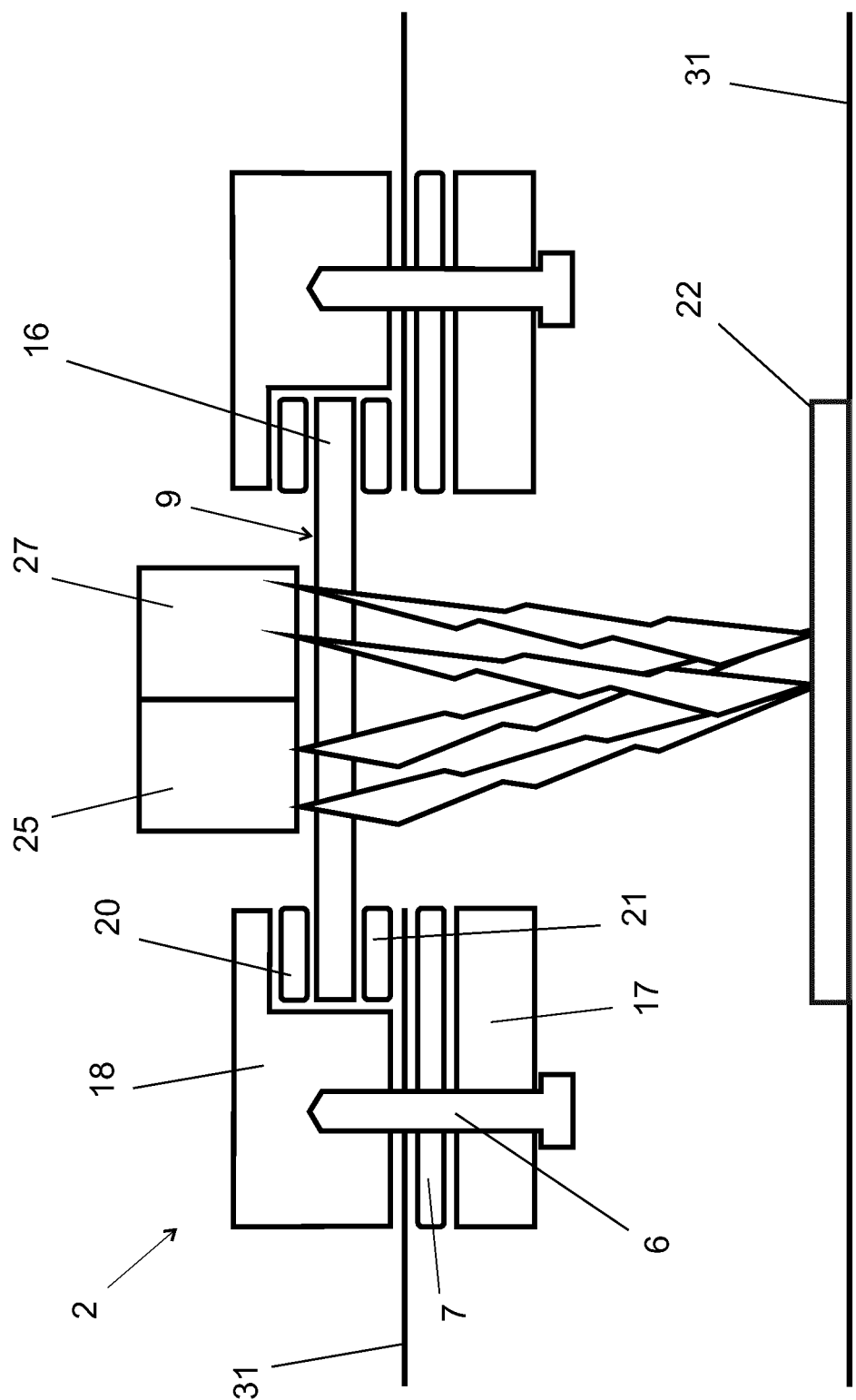

FIGS. 11 and 12 show an example of ozone measurement system that could equip a container according to the invention. As already mentioned, ozone and/or ozonites could be created by irradiating the inside volume of the container 1 through the UV-transparent window 9 of the hollow 2 by means of a Vacuum UV lamp 24. In this example, the container is provided by a mirror 22 that is placed on the bottom of the tray 31. Ozone/ozonites concentration could be determined by irradiating the inside volume by a 240-280 nm wavelength UV lamp and measuring the returning energy of the reflecting rays on said mirror 22. In FIG. 12, a 254 nm UV Lamp 25 is used to irradiate the inside volume of the container and a spectrophotometer 27 to measure such energy.

In an embodiment according to the invention, the window 9 and/or the UV lamp comprises a concave element or another lens, in order to compensate for deviation of the UV rays at the interface between air and such window and to avoid deviation of the rays in undesired directions.

Figure 13:
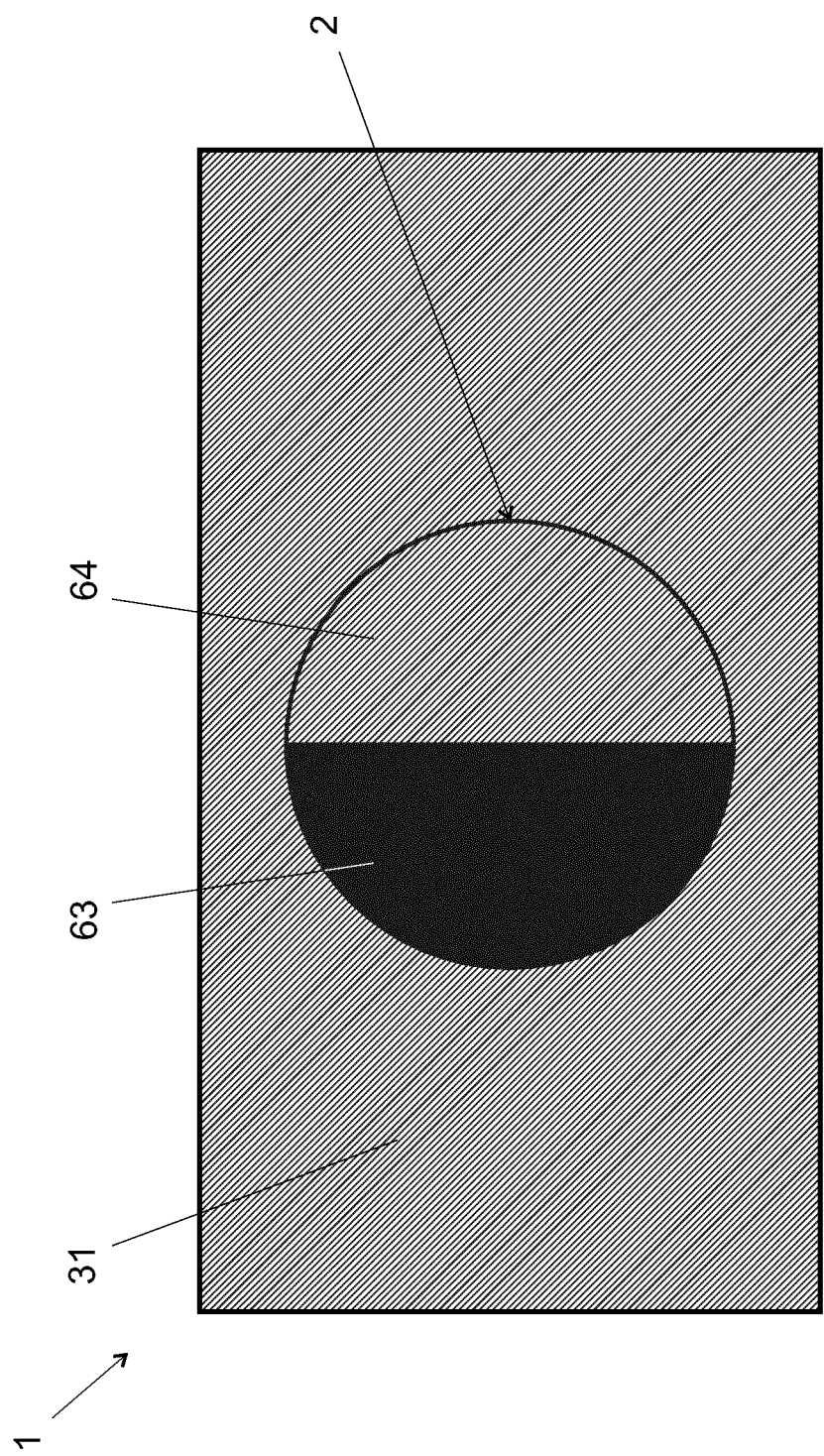

FIGS. 13-15 show an embodiment of a container whose hollow 2 is provided with a shutter (63, 64). The container 1 of this example comprises a tray 31 and a hollow 2. The hollow 2 of this embodiment comprises a shutter with an upper pivoting part 63 and a lower and non-pivoting part 64. The upper pivoting part could pivot from a closed position (FIG. 13) to an open position (FIG. 15). In the open position, the inside volume could be irradiated in order to generate ozone and/or ozonites with a vacuum UV lamp. Ozone/ozonites could be destroyed by irradiating the internal volume by a UVC-middle UV lamp.

In one embodiment, the container could be sealed closing by pivoting the upper part 29 of the shutter in a closed position.

In one independent embodiment, a closable airtight container suitable for storage and sterilization of inside contained medical devices, comprises
an overture in container;
a shutter movable from a closed position to an open position;
wherein such shutter in the open position permits an UV irradiation of an inside volume of the closable container through the overture and/or the insertion of an irradiation part of an UV light source;
wherein the shutter in closed position is adapted to close in an airtight way the overture; and
wherein the rest of the container comprises an Ultraviolet non-transparent material.

In one independent embodiment, a closable airtight container suitable for storage and sterilization of inside contained medical devices comprises:
an airtight closure adapted to introduce such medical devices into the container and adapted to remove such medical devices from the container;
a water tank; and
a window (9) transparent to Vacuum Ultraviolet light and to UVC and/or Middle Ultraviolet light; whereas the rest of said container substantially consists of an ultraviolet non-transparent material.

LIST OF ELEMENTS USED IN DRAWINGS 1 container
2 hollow
3 lid
31 tray
4, 18 outer frame
5, 17 Inner frame
19 fixation
6 screw
7, 8, 20, 2 seal
1
9 UV transparent window
91 closed volume
92 cylindrical UV transparent part
10 UV lamp
11 hole for injection of gas
12 hole for taking out gas
13 irradiating part of the Ultraviolet lamp
14 tube
15 support of the Ultraviolet lamp
150 box
16 UV transparent plate
22 mirror
24 172 nm-UV lamp
25 254 nm-UV lamp
27 spectrophotometer
28 water tank
29 grid
34 vacuum Ultraviolet Light source
35 UVC/Middle Ultraviolet Light source
36 closed container
38 airtight closure
63 pivoting upper part of the shutter
64 lower and non-pivoting part of the shutter
S1-11 steps of sterilization procedures

The invention claimed is:

1. A method of sterilization of a medical device placed in an arrangement comprising a closable airtight container, said container comprising:
an airtight removable lid or an airtight closure for the introduction of said medical device into said container and removal of sterilized said medical device from said container; and
a window transparent to Vacuum Ultraviolet light and to UVC or Middle Ultraviolet light; wherein said window extends over an outside surface of said container that is less than 25 percent of the outside entire surface of said container;
whereas the rest of said container substantially consists of an Ultraviolet non-transparent material;
the arrangement further comprising a computer-operated processing unit configured to trigger and control execution of:
irradiating said volume inside the container with Vacuum Ultraviolet Light through the window of the container so as to generate ozone and/or ozonites within said volume that sterilizes said medical device;
waiting for an incubation time; and
finally, irradiating the volume inside the container with UVC or Middle Ultraviolet Light through the window so as to destroy said ozone and/or ozonites within said volume;
the method comprising the following steps:
a) placing said medical device inside said closable airtight container;
b) closing said container;
c) placing a Vacuum Ultraviolet Light source against a window of said container;
d) irradiating the volume inside said container with Vacuum Ultraviolet Light through said window in order to generate ozone and/or ozonites within said volume;
e) removing said Vacuum Ultraviolet Light source;
f) waiting for an incubation time.

2. The method of claim 1, further comprising the following steps after said step f):
g) placing a UVC or Middle Ultraviolet Light source against said window;
h) irradiating said volume inside said container with UVC or Middle Ultraviolet Light through said window in order to destroy ozone and/or ozonites;
i) removing said UVC or Middle Ultraviolet Light source.

3. The method of claim 1, said container comprising a hollow for a light source,
j) said hollow including said window,
k) wherein said step c) comprises the introduction of said Vacuum Ultraviolet Light source into said hollow.

4. The method of claim 3, wherein said hollow is closed by the introduction of said Vacuum Ultraviolet Light source.

5. The method of sterilization of claim 3, further comprising a step of
   l) Apply vacuum or replacing oxygen by another gas in said hollow, in order to limit the excessive formation of ozone outside of said container.
6. The method of sterilization of claim 1, further comprising a step of
   m) measurement of ozone/ozonites concentration inside said container.
7. The method of sterilization of claim 1, said container being reusable, said method comprising the repetition of steps a) to f) within the same container.
8. The method of sterilization of claim 1, comprising a step of transporting said container to a surgical theatre and opening said container into said surgical theatre in order to access and use the sterilized medical device.
9. An arrangement comprising a closable airtight container for storage and sterilization of inside contained medical devices, said container comprising:
   an airtight removable lid or an airtight closure for the introduction of said medical devices into said container and removal of sterilized said medical devices from said container; and
   a window transparent to Vacuum Ultraviolet light and to UVC or Middle Ultraviolet light; wherein said window extends over an outside surface of said container that is less than 25 percent of the outside entire surface of said container;
   whereas the rest of said container substantially consists of an Ultraviolet non-transparent material;
   the arrangement further comprising a computer-operated processing unit configured to trigger and control execution of:
      irradiating said volume inside the container with Vacuum Ultraviolet Light through the window of the container so as to generate ozone and/or ozonites within said volume that sterilizes said medical devices;
      waiting for an incubation time; and
      finally, irradiating the volume inside the container with UVC or Middle Ultraviolet Light through the window so as to destroy said ozone and/or ozonites within said volume.
10. The arrangement of claim 9, said container further comprising a hollow; wherein said hollow comprises said window and wherein said hollow is adapted to at least partially surround a UV light source.
11. The arrangement of claim 10, wherein said hollow comprises a concave part with at least one UV-transparent side.
12. The arrangement of claim 11, wherein said hollow is substantially cylindrical, conical or tubular.
13. The arrangement of claim 10, further comprising a Vacuum Ultraviolet Light source adapted for removable insertion within said hollow.
14. The arrangement of claim 10, further comprising a UVC and/or Middle Ultraviolet Light source adapted for removable insertion within said hollow.
15. The arrangement of claim 14, wherein said UVC and/or Middle Ultraviolet Light source comprises a fixation that releasably fixes said UVC and/or Middle Ultraviolet Light source to said container in order to place a UVC or Middle Ultraviolet Light source against the window of said container and to build an airtight closed volume between said light source and said window.
16. The arrangement of claim 9, wherein said rest of said container is substantially made of stainless steel, and wherein said window is substantially made of quartz or MgF2 or Ab03 or CaF2.
17. The arrangement of claim 9, said container further comprising a mirror adapted to reflect back ultraviolet light through said window.
18. The arrangement of claim 17, further comprising a spectrometer measuring a returning energy of reflected rays on the mirror.
19. The arrangement of claim 9, comprising a lens for compensating for deviation of UV light at the interface between air and the window.
20. The arrangement of claim 9, further comprising a Vacuum Ultraviolet Light source comprising a fixation that releasably fixes said Vacuum Ultraviolet Light source to said container in order to place the Vacuum Ultraviolet Light source against the window of said container and to build an airtight closed volume between said light source and said window.
21. The arrangement of claim 20, further comprising a gas source for replacing oxygen by another gas in said airtight closed volume, or a vacuum generating means to create vacuum in said airtight closed volume.
22. An Arrangement comprising a closable airtight container for storage and sterilization of inside contained medical devices, said container comprising:
   an airtight removable lid or an airtight closure for the introduction of said medical devices into said container and removal of sterilized said medical devices from said container; and
   a window transparent to Vacuum Ultraviolet light anti to UVC or Middle Ultraviolet light; wherein said window extends over an outside surface of said container that is less than 25 percent of the outside entire surface of said container; wherein said window is arranged so that Vacuum Ultraviolet light entering into said container irradiates a volume inside said container so as to generate ozone and/or ozonites within said volume that sterilizes said medical devices;
   whereas the rest of said container substantially consists of an Ultraviolet non-transparent material;
   the arrangement further comprising a computer-operated processing unit and an identification label;
   wherein the computer-operated processing unit is configured to destroy said ozone and/or ozonites within said volume by triggering and controlling execution of irradiating said volume inside the container with UVC or Middle Ultraviolet Light through the window of said airtight container; and
   wherein the identification label is configured to store data and/or parameters of: a shape and/or a volume of said container, a number and/or a type of inside contained medical devices, an incubation time, and/or the execution of irradiating with UVC or Middle Ultraviolet Light; the identification label being configured to furnish said data to the computer-operated processing unit.
23. The arrangement of claim 22, said container further comprising a hollow; wherein said hollow comprises said window and wherein said hollow is adapted to at least partially surround a UV light source.
24. The arrangement of claim 23, wherein said hollow comprises a concave part with at least one UV-transparent side.
25. The arrangement of claim 23, wherein said hollow is substantially cylindrical, conical or tubular.

26. The arrangement of claim 23, further comprising a Vacuum Ultraviolet Light source adapted for removable insertion within said hollow.

27. The arrangement of claim 26, wherein said Vacuum Ultraviolet Light source comprises a fixation that releasably fixes said Vacuum Ultraviolet Light source to said container in order to place the Vacuum Ultraviolet Light source against the window of said container and to build an airtight closed volume between said light source and said window.

28. The arrangement of claim 27, further comprising a gas source for replacing oxygen by another gas in said airtight closed volume, or a vacuum generating means to create vacuum in said airtight closed volume.

29. The arrangement of claim 23, further comprising a UVC and/or Middle Ultraviolet Light source adapted for removable insertion within said hollow.

30. The arrangement of claim 29, wherein said UVC and/or Middle Ultraviolet Light source comprises a fixation that releasably fixes said UVC and/or Middle Ultraviolet Light source to said container in order to place a UVC or Middle Ultraviolet Light source against the window of said container and to build an airtight closed volume between said light source and said window.

31. The arrangement of claim 22, wherein said rest of said container is substantially made of stainless steel, and wherein said window is substantially made of quartz or MgF2 or Ab03 or $CaF_2$.

32. The arrangement of claim 22, said container further comprising a mirror adapted to reflect back ultraviolet light through said window.

33. The arrangement of claim 32, further comprising a spectrometer measuring a returning energy of reflected rays on the mirror.

34. The arrangement of claim 22, comprising a lens for compensating for deviation of UV light at the interface between air and the window.

* * * * *